United States Patent [19]

Prusik et al.

[11] Patent Number: 5,057,434
[45] Date of Patent: Oct. 15, 1991

[54] MULTIFUNCTIONAL TIME-TEMPERATURE INDICATOR

[75] Inventors: Thaddeus Prusik, Roosevelt; Raymond M. Arnold, Harrisonville, both of N.J.

[73] Assignee: LifeLines Technology, Inc., Morris Plains, N.J.

[21] Appl. No.: 400,308

[22] Filed: Aug. 29, 1989

[51] Int. Cl.$^5$ .................. G01N 31/22; B05D 1/00
[52] U.S. Cl. ..................... 436/2; 116/207; 116/208; 116/217; 252/408.1; 422/56; 422/57; 422/58; 427/2; 436/7
[58] Field of Search .................. 422/56–58; 436/2, 7; 116/207, 208, 217; 252/408.1; 427/2

[56] References Cited

U.S. PATENT DOCUMENTS

| | | | |
|---|---|---|---|
| 3,999,946 | 12/1976 | Patel et al. | 422/56 |
| 4,154,107 | 5/1979 | Giezen et al. | |
| 4,382,700 | 5/1983 | Youngren | 116/216 X |
| 4,533,640 | 8/1985 | Shafer | |

Primary Examiner—Jill Johnston
Attorney, Agent, or Firm—Arthur J. Plantamura

[57] ABSTRACT

An accurate monitoring of the conditions of a perishable product is achieved by integrating two indicator types - a primary indicator which develops a color change as a result of cumulative time-temperature exposure and a threshold second indicator - into a single device. The combination of the two indicators in the same indicator device provides a human readable signal that gradually and irreversibly develops color as a function of time and temperature and more closely monitors the actual condition of a deteriorative product than does a single indicator. Important features of this integrated monitoring device are reliability and printability. The primary indicator in the system is assisted in color development by the secondary indictor that is set to trigger at a predetermined temperature. When this temperature is reached or exceeded both indicator mechanisms function in an additive mode to cause a break in the typical Arrhenius curve, which a primary indicator alone produces. This can be used to signal actual rather than an apparent the end of a product life. The secondary indicia can be formulated to change very rapidly as would be needed to detect the thawing of a frozen product or modified so as to act more slowly, i.e. over at time-temperature range, and may comprise a substance that melts or changes some physical property at a given temperature.

18 Claims, 3 Drawing Sheets

MULTIFUNCTIONAL TIME-TEMPERATURE INDICATOR

The present invention relates to an improved time-temperature indicator device useful in monitoring the environmental exposure of products that undergo progressive quality changes in response to such exposures.

BACKGROUND OF THE INVENTION

With the increased attraction of convenience (already at least partially prepared and packaged) foods, especially the fresh or non-frozen foods, that appeal to a modern age populus, the hazards of illness from spoiled food has increased. As distinguished from frozen or cooked products, such foods require a substantially greater degree of control. Aggravating the problems of controlling the quality of such food is the fact that such food may actually be spoiled and such spoilage can go undetected because no foul odor is detectable. Many of these new convenience foods that are being introduced into the market are chilled products that are packaged in a modified atmosphere and contain no preservatives. This creates a potential problem for the manufacturers, distributors, and consumers of these products—a product that is temperature abused can look, smell and taste wholesome, but can be toxic. The only way that such products can be kept safe is to maintain strict temperature control of the product during its entire shelf life. Since it is well known that temperature abuses occur during distribution, an indicia that gives some measure of the intrinsic wholesome quality of a product that is read by the human eye will be of extreme value in guaranteeing the wholesomeness of the product.

While many attempts have been made and various patents have been issued dealing with devices designed to be attached to a package and to show when a package has been temperature abused or has reached the end of its useful shelf life, none is known that is sufficiently adaptable to closely monitor the deterioration of a particular product. For example, an active indicator element can be an acetylenic compound that changes color, an enzyme/substrate system with a pH indicator that changes color, or a dyed wax that diffuses along a strip of paper, to name several. The indicator can be interpreted by visual comparison of the indicator section to a stable reference color(s), or messages can be made to appear from the background. Some indicators rely on electro optical scanning of the indicator, measurement of the indicator resistance, or other machine readable output. Some such methods show how to make a device that changes color when exposed to a cumulative time-temperature exposure. In general, the higher the temperature, the faster the rate of color change and the faster the indicator would signal the end of the life of the product. U.S. Pat. No. 3,999,946, for example, teaches the use of the solid-state polymerization of acetylenes as full time-temperature history indicators. Full time-temperature history indicator composites that are particularly useful for monitoring the shelf lives of perishable products are disclosed in U.S. Pat. No. 4,788,151. The indicator compositions describe therein are shown to be useful in monitoring the shelf lives of products from days to years at room temperature, and from days to years at refrigerated temperatures. In addition, it is shown that these compositions can be formulated into conventional ink systems and printed.

Other methods of preparing full time-temperature history indicators include: U.S. Pat. No. 3,768,876 which incorporates a redox dye in its reduced state (red), that oxidizes as a function of time and temperature in an atmospheric environment and becomes colorless; U.S. Pat. No. 4,292,916 which describes carrier mixtures and receptive layers that react during a given time interval; U.S. Pat. No. 4,212,153 which describes a laminated indicator with at least two layers that gives rise to a perceptible color due to the molecular migration of an agent from an inner layer so an external layer; U.S. Pat. No. 3,344,670 which describes the use of silver nitrate on a bleached paper together with a color comparator to signal integral time-temperature exposures that follow Arrhenius kinetics; and U.S. Pat. No. 3,966,414 which describes the combination of free radical sensitive dyes and peroxides to prepare time-temperature integrators with varying activation energies. The basic similarity and mechanism of action of all previous technologies is for a section of the indicator to change in some single measurable property, due to physical and/or chemical change(s). Indicators are basically grouped into two families, those which signal a change only after a certain critical temperature has been reached or exceeded and those which integrate over the entire temperature range and signal a condition at any stage. The simplest embodiment of the secondary indicator, one which begins to signal above a predetermined temperature, is to have a heat meltable material within which is described a colored dye. When this layer is printed behind the primary indicator system and kept below its melt point, then no migration of the heat fusible layer takes place and hence, no color is developed. Above the melting point of the material, the dyed layer will be mobile and will cause color to be developed in the observed layer. It may be advantageous to have the heat fusible layer and the secondary indicator layer be individual components of a co-reactant pair that gives rise to color. This could be through the use of pH sensitive materials, oxidizable or reducible dyes, organic molecules with functional groups that react to form or change color, metal ions and chelating agents, or the like. A preferred embodiment of the secondary indicator system is one in which a water soluble dye is dispersed in a solvent based ink. This dye system is essentially colorless, or only lightly colored, until it is contacted with a hydrophilic solvent for the dye composition. Once contacted with the hydrophilic solvent, the dye dissolves and produces a bright color in the visible layer. Convenient dyes include FD&C approved dyes. A preferred heat fusible material that solubilizes these dyes is polyethylene glycol (PEG). PEG comes in a variety of molecular weights. The higher the molecular weight the higher the melt point of the system. Virtually any melt point from freezer temperature through 52° C. can be obtained by mixing different proportions of different PEG's. Methods of preparing indictors that react above a predetermined temperature are described in U.S. Pat. Nos. 4,432,656; 4,643,588; 3,065,083; 4,057,029; and 3,967,579. Although descriptions of many different concepts and methods of preparing indicators have been published, only a limited number of such systems have received any commercial interest.

Of the available technologies that have attained some practical utility, none address the problem in a sufficient manner. In general, most chemical reactions leading to the loss of quality of a product follow an Arrhenius-type temperature dependence. This is true of most of the time-temperature sensitive devices described in the literature. As shown in the drawing and described hereafter, an Arrhenius-type plot of the time for a certain indicator to read a particular color as a function of time and temperature has been illustrated. However, it is known that in many instances that the growth rate of microorganisms does not follow a strictly Arrhenius temperature dependence, and in fact some microorganisms do not grow below a certain temperature in the chill range. Organoleptic and/or textural properties of the product would limit the useful life of a product when stored under proper refrigerated conditions. Also shown by comparison is an illustration of a specific product, i.e. raw fish by way of example, and the time to toxin production for such raw fish stored in a modified atmosphere. The data show that the temperature dependence of the reaction for this particular product is clearly non-Arrhenius (non-linear on the plot). Thus, a device that follows an Arrhenius relationship would not be adequate to monitor the storage conditions of a product when the quality of whose temperature dependence is clearly non-Arrhenius (non-linear on the plot). The superposition of the curves of the two data sets illustrate areas of disparity of the actual condition relative to the theoretical (Arrhenius curve) and show that products stored at the proper temperature would be prematurely signaled as having reached the end of the shelf life well before the actual end of the life of the product, thus causing a perfectly good product to be unnecessarily discarded. Even if the slope of the line is changed by varying the mode of action of the device, there will be an unsatisfactory compromise between the indicator response and the end of the useful or safe life of the product.

Another known indicator is that described as a dyed wax device. This indicator is comprised of a dyed wax that melts at a certain temperature and migrates down a wick to signal the amount of time above a threshold temperature. An indicator such as this could be used to signal high temperature abuse, but would give no practical signal during long term proper cold storage. Thus, a properly stored product using this type of indicator would never be shown to be spoiled, even though all chilled products have a finite lifetime during cold storage. In general this type of diffusion process is not very temperature sensitive and has a shallower slope on the Arrhenius plot.

SUMMARY OF THE INVENTION

It is thus seen that a need exists for a more accurate and reliable device that produces an indication that is closely attuned to the intrinsic quality of a product being monitored.

The invention utilizes the concept of using a system of two different indicator technologies to give a single output that can be more closely correlated to the quality condition of a product than either system alone. This is accomplished by the additive nature of the two distinct indicator processes to yield a single visual output. This feature cannot be accomplished by using two physically separate indicators because the desired visual effect of the combination of systems of the current invention is essentially additive and differs from the results obtained by observing two physically distinct indicators.

This invention is novel because it allows for non-Arrhenius kinetics to be monitored by a single device and takes into account the effect on the indicator during both long term storage at proper temperatures and short term high temperature exposures to signal expiration of a product. This is accomplished by combining two indicator types, i.e. two systems,—an integrating indicator (a) and a threshold indicator (c)—into a single device to give one output. The first indicator (a) acts independently. The second indicator composition (c) may comprise a separate layer or it may be mixed with the indicator (a) and held inactive until the predetermined "release" temperature of (b) is reached at which time (b) composition is permitted to contact and influence the color change that has occured in the observed layer as a consequence to environmental temperature change. The importance of the combination of the two devices integrated as an entity in the same indicator is to make the performance signal from the two device system immediately detectable to an observer. On the other hand, an indicator with multiple, i.e., discrete, elements positioned next to each other would necessitate the user to read and interpret multiple, relatively complicated directions and would undoubtedly frequently lead to confusion in the intended purpose of the indicia, thereby rendering the device impractical for many uses.

In a preferred embodiment which is illustrative of the invention, diacetylenic monomers are printed on a transparent film as the primary indicia of long term proper storage of the product. As a function of time and temperature the material gradually and irreversibly develops color. When the indicator labeled product is held at proper, i.e. designated, storage temperatures, the product and its associated indicator would expire simultaneously as shown by the environmentally responsive color changeable indicator section as it matches in color to the printed, temperature stable reference color.

Important features of the system of this invention include: reliability and printability. These are critical parameters. Reliability is needed to make the signaling device and, thereby, the quality of a product associated therewith, a practical tool. Printability translates to the exonomics and affordability for retail labeling.

The primary indicia of the combined indicator system of the invention is assisted in color development by having a secondary indicator that is set to trigger at a predetermined temperature. When this predetermined temperature is reached or exceeded, both indicator mechanisms of the combined system function in an additive mode to cause a break in the Arrhenius curve and signal a critical condition, e.g. the end of the product life, more rapidly than would the individual components of the indicator. The secondary indicia can be made to change very rapidly. Such a system would be desired, for example, to detect the thawing of a frozen product, or the melting of a chocolate confectionary. The secondary indicia could be made to change more slowly such as in the case of the deterioration in quality of the above cited chilled food product. This secondary indicator necessitates the incorporation into the indicator (of the combined indicator system) of an ingredient that melts or changes some physical property at a desired given temperature. In the combined indicator, the summation of the slowly developing color and in combination with the color induced by "abuse", i.e., exposure, above a predetermined temperature, will signal the end of the shelf life before safety of the product is a concern.

DETAILED DESCRIPTION OF THE INVENTION

Figure 1:
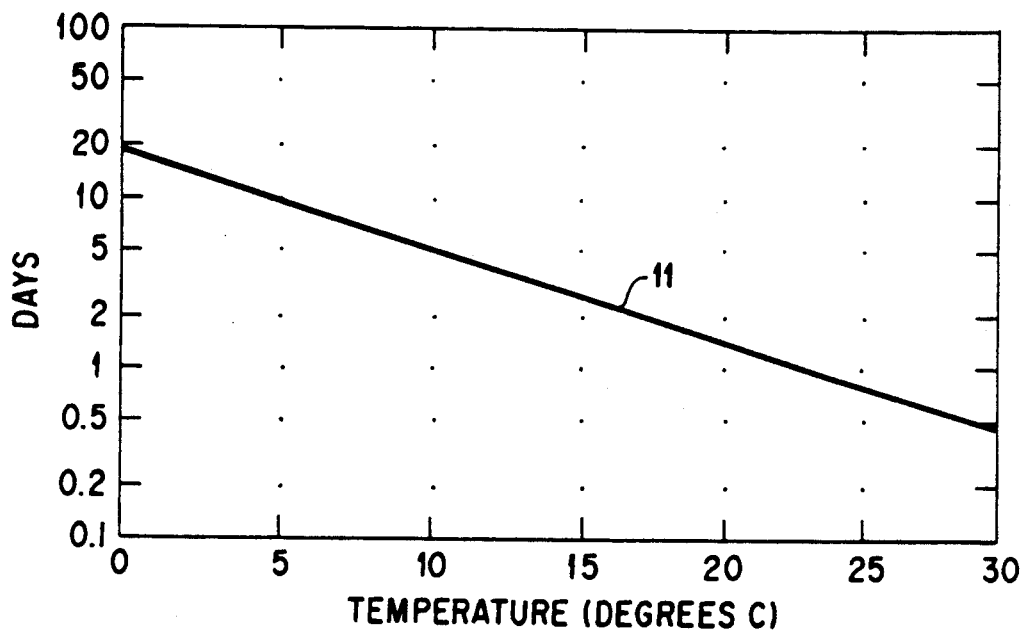
FIG. 1 Illustrates an Arrhenius-type curve of the time for a typical full history time-temperature indicator to reach a given color as a function of storage temperature. The linearity of the plot depicts conformance to the Arrhenius relationship.

Because known time-temperature indicators typically reflect chemical reactions that follow an Arrhenius-type temperature dependence or react only above a certain threshold temperature, such may be, and frequently are, unsuitable to accurately indicate the conditions of a product whose plot of change in characteristic, e.g. spoilage of the product, is non-Arrhenius. The invention addresses this problem and provides an improved indicator which deviates from the Arrhenius regimen and which relatively closely traces the actual change in the intrinsic condition of a product which is exposed to environmental stimuli. The novel indicator system of the invention takes into account both long term storage at proper temperatures and short term high temperature excursions to signal expiration of product. This is accomplished by combining two indicator types—an integrating indicator and a threshold indicator—into a single indicator device. The novel result of the combination of the two devices in a single indicator is to make the signal immediately obvious to an observer. An indicator with multiple discrete elements positioned next to each other and functioning independently on the other hand would necessitate the user to read and interpret complicated directions and would likely lead to confusion in the interpretations of the multiple indicia rendering the device substantially impractical.

In accordance with the invention two different indicators, selected for their specific performance when they are combined, i.e. integrated, are used to yield a single output that more closely vollows the condition of a product as it responds to the effects of the ambient environment. The invention is accomplished by the incorporation into the indicator system of the invention a plurality, i.e. at least two, functional layers which respond the the environment. In the system, one of the layers may be active at inception; another layer may include a means to trigger the activation of at least one other layer resulting from a condition that develops as the multilayer indicator undergoes environmental exposure. To illustrate, a device can be fabricated, for example, with a diacetylene material, printed to expire after 21 days at 3.3° C. This device alone would allow a food producer to get the full shelf life from the product provided it is kept under good temperature control. If this was the only functioning portion of the device, then it is apparent that the indicator would not signal a condition warning at temperatures above about 6° C. To assist in additional color development a material with a melting point of about 6° C. can be used with a dye, or chemical in a second layer. At temperatures below the melting point of the material, the dyed material or chemical will be immobile and not add to the color. However, at temperatures above the melting point, the material becomes mobile and will diffuse through the layers and add color to the indicator. Thus, a device can be devised that will allow full shelf life of the product at proper storage temperatures and signal temperature abuse at short time at elevated temperatures. The same result cannot be accomplished by using two physically separate indicators because the visual effect of the present invention is additive and differs from the separate results.

The advantage of the invention thus resides in the provision of a novel system that allows for non-Arrhenius kinetics to be monitored by a single integrated device. For example, printing and using a diacetylenic monomer containing composition or another known time-temperature indicator, on a transparent film as the primary indicia of long term proper storage of the product, as a function of time and temperature, the material gradually and irreversibly develops color. Where the product is held at proper storage temperature, the indicator and product would expire simultaneously. This primary indicia, sometimes referred to as composition (a), is assisted in color development through the use of a secondary indicator. The secondary indicator, containing a composition (c), is set to trigger, e.g. melt, at a predetermined temperature range. As this temperature is reached, or exceeded, it initiates a color forming change as a result of the dissolving of a dye composition (b); both the indicator mechanisms of (a) and the dissolution of (c) function in an additive mode to cause a break in the Arrhenius curve and signal the end of the product life. This secondary indicia represented by the activity of meltable composition (b) can be made to change very rapidly as would be needed to detect the thawing of a frozen product or much more slowly, i.e. over a range, as in the case of the above cited chilled food product and comprises a substance that melts or changes some physical property at a given temperature. Various substances that are known to function in the manner of the secondary indicator may be integrated into the indicator system of the invention such that the results of the slowly developing color and color induced by the short term abuse will clearly signal the end of a safe and acceptable shelf life. The invention will be further described by reference to the drawings.

Illustrative primary time-temperature indicator compositions (a) which may be utilized with composition (b) and (c) to provide the system of the invention include acetylenics, spiropyrons, enzymes and pH indicators, preradical sensitive dyes and peroxides, triarylmethane dyes, polymethine dyes, azo compounds, azomethine compounds alkali metal salts, alkaline earth solids, and alkali metal azides. Examples of these generic classes of compounds include: 5,7-dichloro-6-nitro-BIPS (BIPS=1',3',3'-tri-methylspiro-[2H-1-benzopyran-2,2'indoline]), 6-chloro-8-nitro BIPS, 7-nitro BIPS, Malachite Green, Crystal Violet, Pararosaniline, 4-dimethylaminoazobenzene, 4-nitroazobenzene, azobenzene, 1,2-naphthoquinone-2-diphenylhydrazone, sodium chloride, potassium chloride, potassium bromide, La doped $CaF_2$, Ce doped $CaF_2$, Gd doped $CaF_2$, $KN_3$, and $NaN_3$.

The following are illustrative of the meltable composition (b) which may be employed.

MELTABLE MATERIALS
Substitutes for PEG
Oleic Acid
Stearic Acid
Myristic Acid
Paraffin Waxes
Polyvinyl Ether Wax (V Wax ex. BASF)
Polyethlene Waxes
Polyethlene Glycols
Polyamide Resins
Cyclohexanone Resins
Low Molecular Weight Acrylic Resins
Cetyl Palmitate (Spermaceti)
Sorbitol
Carnauba Wax
Castor Wax
Micro Crystalline Wax
Ceresine Wax
Ethyl Myristate
Dimethyl Adipate
Ethyl Cinnamate
Ethyl Nicotinate
Methyl Laurate
Water
Di Phenyl Phthalate
N-Ethyl-Toluene Sulphonamide (Santiciser 8) Monsanto
Benzyl Phthlate Mixtures of these compositions may be employed in the practice of the invention.

The secondary color forming indicator composition (c) may include such as dyes both water soluble and water insoluble, pH indicators; free radical dyes in combination with a peroxide, oxidizable or reducible dyes, organic molecules with functional groups that react to form or change color, metal ions and chelating agents, or the like. Indicator dyes can be used from the following list:

Water Soluble Dyes
FD&C Blue #1, #2, #3, Red #3, Yellow #5, Yellow #6, Red #40
Metanil Blue, Metanil Yellow
Safronine O, Celestine Blue, Acid Blue 4
Acid Violet, Sandarin Blue
Brilliant Blue G, Crystal Violet
Indicators
Bromo Thymol Blue, Phenol Red
Bromo Cresol Purple
Bromo Cresol Blue
Methyl Orange, Congo Red
Solvent Dyes Soluble in Waxes, etc.
Oil Blue N, Solvent Green
Methyl Violet B
Oil Red O, Sudan Orange Mixtures of these compositions may be employed in the practice of the invention.

As seen in FIG. 1, an Arrhenius-type plot is shown of the time for an indicator, (Model A40, available from LifeLines Technology, Inc., Morris Plains, N.J.), to reach a certain color as a function of storage temperature. The linearity of the plot which is shown in line 11 conforms substantially to an Arrhenius relationship. FIG. 1 demonstrates, essentially, the prior art indicator performance for a full time-temperature history indicator.

Figure 2:
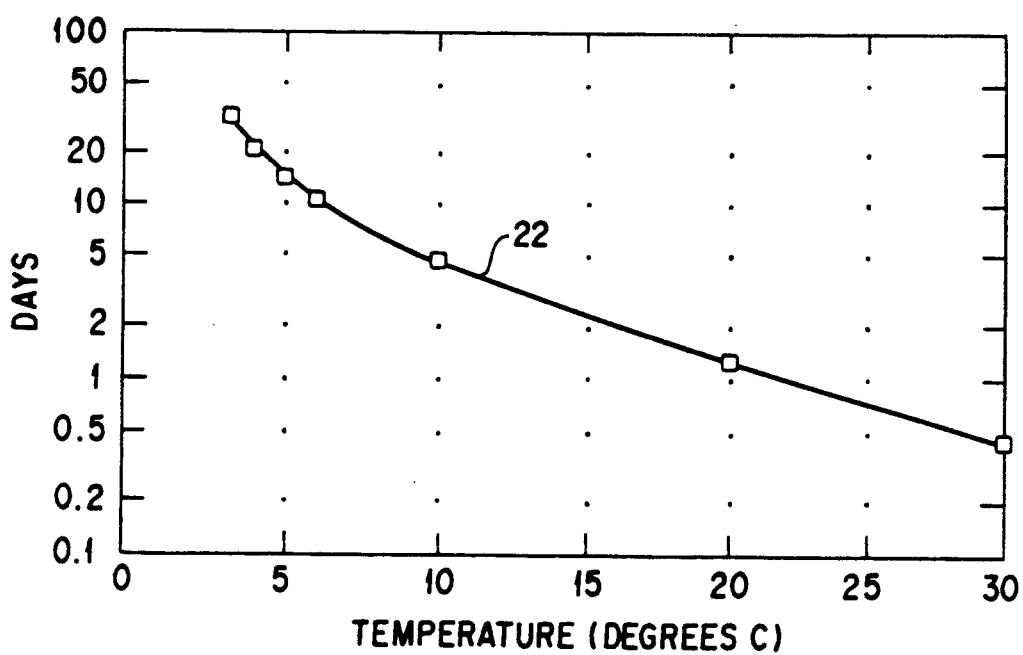
FIG. 2 Illustrates the actual line of the usable life of a product, i.e., the product line demonstrates time to toxin production for raw fish stored in a modified atmosphere. The data show that the temperature dependence of the reaction is clearly non-Arrhenius (non-linear on the plot).

In FIG. 2, the actual quality condition of raw fish exposed to the temperature environment indicated on the chart is plotted and by line 22 shows time to toxin production for raw fish stored in a modified atmosphere. The data show that the temperature dependence of the reaction is clearly non-Arrhenius, i.e., on the plot is non-linear.

Figure 3:
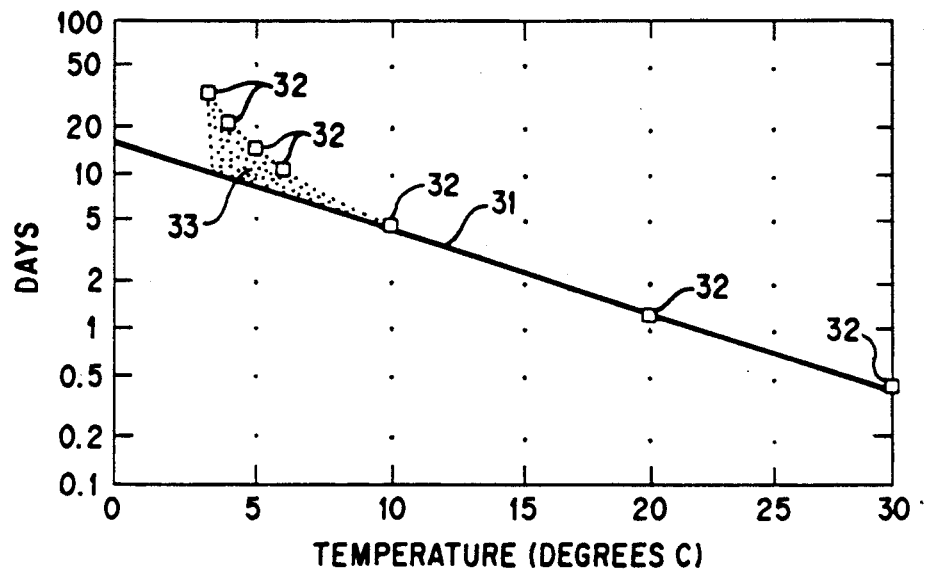
FIG. 3 Shows a superposition of the two data sets from FIGS. 1 and 2 and demonstrates some areas in which the actual condition is not signaled by the Arrhenius curve, such that, for example, at temperatures less than 12° C., the indicator will show that the product is no longer wholesome before toxigenesis while at temperatures greater than 12° C., both the product and indicator reach their respective endpoints simultaneously.

FIG. 3 combines the showing of the data of FIG. 1 and FIG. 2. The line 31, the Arrhenius curve, shows when the time-temperature indicator signals the expiration of the shelf life by matching in color to the printed stable reference color along the length of line 31. The points 32 show when the product has deteriorated so that its use is unsafe. At temperatures less than 12° C., shown by the shaded area 33, the indicator shows that the product is no longer wholesome before toxigenesis; however, at temperatures greater than 12° C., a product and indicator so stored would expire at the same time. It can be seen that products stored at proper temperatures (below about 5° C.) would be signaled by the color change of the indicator as having reached the end of the shelf life well before the actual end of the life of the product. Since this is the reading that would result if the Arrhenius pattern were to be controlling, it would result in the premature discarding of a perfectly good product. It is to be noted also, that the growth rate of microorganisms does not follow a strictly Arrhenius temperature dependence, and in fact some microorganisms do not grow below a certain temperature in the chill range. Organoleptic and/or textural properties of the product would limit the useful life of a product when storaged under proper refrigerated conditions. For these reasons, a device that follows an Arrhenius relationship would not be adequate to monitor the storage conditions of the various products that do not follow the Arrhenius relationship.

Figure 4:
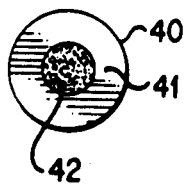
FIG. 4 Illustrates one form of the indicator of the invention prepared in the form of a spot on a label which may be attached to a product whose quality is to be monitored.

The multilayer indicator system of the invention may take various forms. Two variations of the visual appearance of indicators of the kind which may be affixed to a product as those depicted in FIG. 4 and FIG. 5. FIG. 4 shows a circular label 40 having a conveniently sized outer contrasting area 41 and a smaller substantially centered smaller area 42 of contrasting color. Although the indicator portion is that shown as 42, it is apparent that the roles may be reversed and alternatively the area 42 may comprise the layers of indicator composition.

Figure 5:
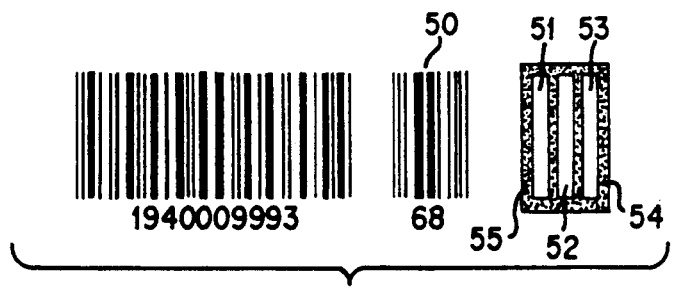
FIG. 5 Illustrates an alternate form of the indicator of the invention comprising a a strip of the composition of the invention that may be added on to a conventional bar code type label which may be affixed to a product.

FIG. 5 shows an indicator of a different format which comprises a label 50 in the form of a conventional bar code in which the indicator layer system comprises a bar 52 which is separated by spaces 51 and 53 from stop/start bars 54 and 55.

Figure 6:
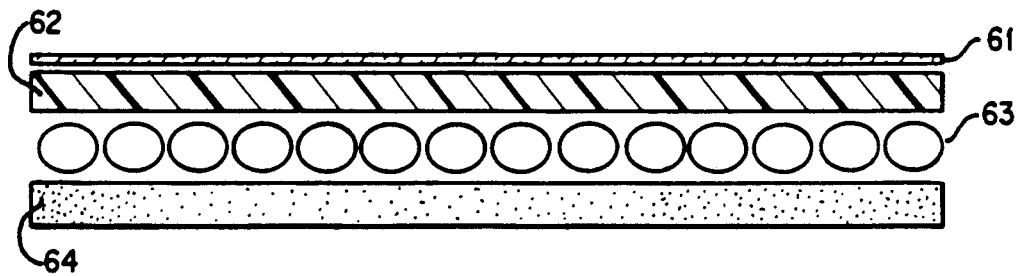
FIG. 6 Illustrates in enlarged cross-section one form of the multilayer time-temperature indicator system in accordance with the invention.

Referring to FIG. 6, one embodiment of the invention is illustrated although a variety of embodiments of the invention may be used to accomplish the intended purpose of the device. The simplest version is a label comprised of several layers including: a transparent film 61; a color developing primary indicator material 62, e.g., a diacetylene material, a color forming system that responds to the action of layer 62, binders and fillers; a material 63 capable of undergoing a transformation at a predetermined temperature or over a narrow temperature range; a backing layer 64, which contains an adhesive to hold the device together and a self adhesive with a release liner for attachment to a product. The layer 64 may function in a dual capacity, to seal the indicator and to provide a means from attachment of the indicator to the article being monitored.

Figure 7:
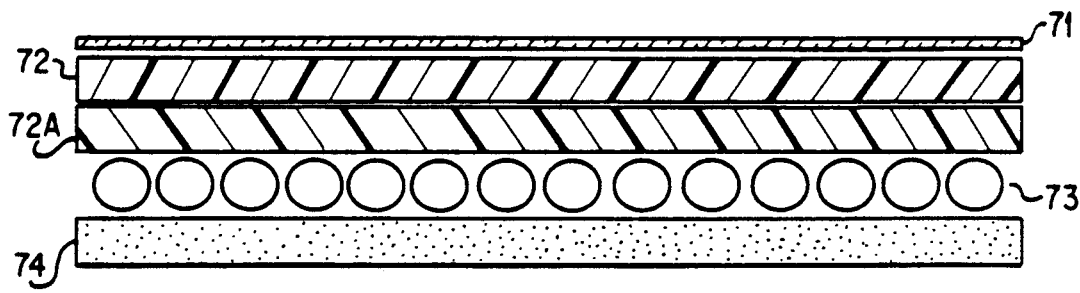
FIG. 7 Illustrates in enlarged cross-section a modified multilayer time-temperature indicator system in accordance with the invention.

Referring to FIG. 7, another embodiment is illustrated as being amenable to a variety of time-temperature schedules that may be addressed by the invention and the inherent limitations of ink formulations with the requisite physical characteristics to be suitably response as time-temperature indicators. The capabilities of the system can be enhanced firstly by the physical separation of layers 72 and 73 by a barrier layer 72A that delays the action of layer 73 on the receptive material of layer 72. Modification of the barrier layer 72A with different resins and additives changes the time required for the first observation of change in indicator color and continuing color development of the combined action of layers 72 and 73. Layer 74 functions in a manner analogous to that decribed above for layer 64 in FIG. 6.

Figure 8:
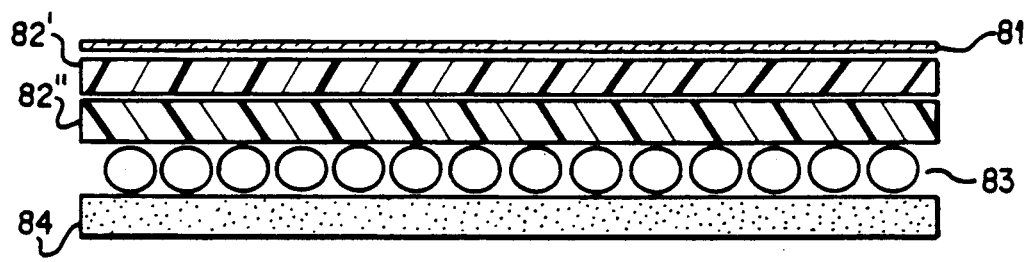
FIG. 8 Illustrates in enlarged cross-section still another embodiment of the time-temperature indicator system in accordance with the invention.

Referring to FIG. 8, the system of the invention can further be modified by separating the primary and secondary indicator layers. This allows formulation of an ink with variable color development properties for the secondary indicator.

Figure 9:
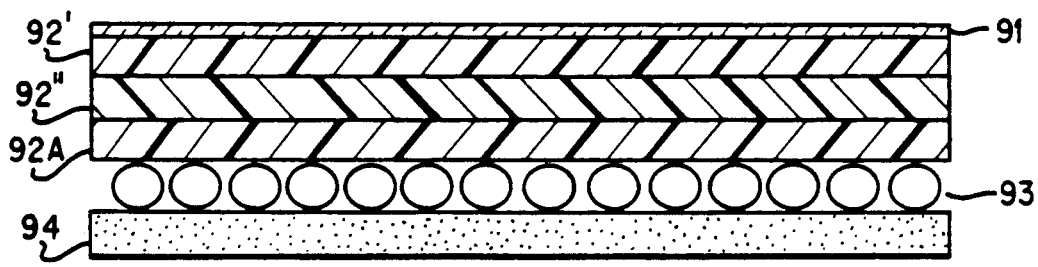
FIG. 9 Illustrates in enlarged cross-section a further embodiment of the time-temperature indicator of the invention.

Referring to FIG. 9, introduction of the barrier layer into the arrangement with FIG. 8 introduces an additional delay in the color response of layer 93 on the secondary indicator material.

It is thus seen that the combination system of the invention allows for non-Arrhenius kinetics to be monitored by a simple device. Such device can be fabricated, for example, with a diacetylene material or the like, that is printed to expire after 21 days at 3.3° C. A device of this kind alone would allow the food producer to get the full shelf life form the product provided it is kept under good temperature control. If this was the only functioning portion of the device, it is seen by reference to FIG. 6 that the indicator would not signal a conservative warning at temperatures above about 6° C. To assist in additional color development a material with a melting point of about 6° C. can be used with a dye, or chemical in layer 62 above. At temperatures below the melting point of the material the dyed material or chemical will be immobile and not add to the color. However, at temperatures above the melting point, the material will be mobile and diffuse through the layers 93 and/or 94 and add color to the indicator. Thus, a device is made that will allow full shelf life of the product at proper storage temperatures and signal temperature abuse at short time at elevated temperatures.

The invention will be described in further detail by reference to the following specific examples. The enumeration of details should not be construed as a limitation on the invention except as may be set forth in the accompanying claims.

EXAMPLE 1

A multilayer device as shown in FIG. 6 was prepared by combining primary and secondary indicator compositions, binders and fillers as layer 62. The wet ink formula by weight was 51 parts of a 10% solution of Klucel (Hydroxy propyl cellulose, Type EF, Aqualon Co.); 17 parts of a cocrystallized mixture of 2,4-hexadiyn-1,6-bis (ethyl urea) and 2,4-hexadiyn-1,6-bis (n-propyl urea) at a mole rate of 2:1, 6 parts of 4% FD&C blue No. 1 suspension in 7 parts of 50% titanium dioxide (R900, Du Pont Corp.), 10 parts china clay (English Colloidal Kaolin, Whittaker, Clark & Daniels) and 15 parts cyclohexanone. Quarter inch diameter circles were screen printed similar to the illustration of FIG. 4, on a 2 mil clear polyester film depicted as 61 in FIG. 6, using the above ink and a T40 monofilament polyester fabric. Polyethulene glycol (PEG) (E3350 Dow Chemical Co.,) having a melting point of 54° C. was heated to 60° C. and a thin coating of the molten material was applied to the printed layer (61). The PEG rapidly solidified forming layer (63). Polyart 2 backing layer (64) was applied to the back of the printed dots. The adhesive of layer 64 seals around the printed image and effectively encapsulates the device and prevents the migration of the PEG when melted. These multilayed devices were placed at 65° C. and periodically removed from the temperature controlled chamber for inspection. The color of the indicator was measured with a MacBeth PCM2 reflectance meter set on Filter E. Control sample without layer 63, the heat fusible layer), were also placed in the same temperature controlled chamber. The results of the test are summarized in Table I.

TABLE 1

| TIME (MINUTES) | REFLECTANCE METER READINGS | |
| --- | --- | --- |
| | WITH PEG 3350 | WITHOUT PEG |
| 0 | 67 | 67 |
| 5 | | |
| 10 | | 64 |
| 15 | | 61 |
| 20 | 48 | 58 |
| 25 | | |
| 30 | 44 | 55 |
| 35 | | |
| 40 | 41 | 52 |
| 50 | 37 | 47 |
| 60 | 33 | 45 |
| 70 | 33 | |
| 80 | | |
| 90 | 31 | 40 |

This example shows that the dual function indicator system develops color more quickly than the primary indicator system above the melting point of the PEG. The control sample without PEG shows the cumulative effect of time and temperature on the primary indicator system alone. With PEG in the system and the two indicator systems functioning together, the time to reach 40% reflectance is approximately reduced to half.

EXAMPLE II

The same indicators from Example I were prepared with one exception. Layer 63, the heat fusible layer, was formed with polyethylene glycol PEG 600 (Dow Chemical Co.). This PEG layer has a lower molecular weight and lower melting temperature (22° C.) than the PEG 3350. At 65° C. this PEG is very fluid and produces in the combined indicator a more rapid change in the secondary indicator system. Table II includes also the results from Example I for comparison.

TABLE II

| TIME (MINUTES) | REFLECTANCE METER READINGS | | |
|---|---|---|---|
| | WITH PEG 3350 | WITHOUT PEG | WITH PEG 600 |
| 0 | 67 | 67 | 67 |
| 5 | | | 45 |
| 10 | | 64 | 40 |
| 15 | | 61 | |
| 20 | 48 | 58 | 38 |
| 25 | | | |
| 30 | 44 | 55 | |
| 35 | | | |
| 40 | 41 | 52 | 28 |
| 50 | 37 | 47 | |
| 60 | 33 | 45 | |
| 70 | 33 | | |
| 80 | | | |
| 90 | 31 | 40 | |

EXAMPLE III

Devices as shown in FIG. 7 were prepared. The primary and secondary indicators were printed in layer 72 and a barrier layer 72A was printed over this material to show the migration of the heat fusuble material and thus show the rate of color change of the secondary indicator system. Layer 72 was composed of 10.0% of a co-crystallized mixture of 2,4-hexadiyn-1,6 bis (ethyl urea) and 2,4-hexadiyn-1,6 bis (n-propyl urea) in a 2:1 mole ratio; 10% of a 50% B67 (Rohm & Haas) resin solution in Solvent 150 (Exxon); 13.9% of a 40% F10 (Rohm & Haas) resin in 90/10 mineral spirits/solvent 100; 14.8% China Clay; 7.5% of a solution of chlorinated rubber (Alloprene) (I.C.I.); 0.13% brilliant blue G dye, 4.1% titanium dioxide (Du Pont) R900; 35.9% solvent 150 (Exxon); and 2% flow agent (Fx 32) (I.C.I.). This ink was printed on a 2 mil clear polyester film with a T40 mesh polyester fabric screen.

The barrier layer 72A was prepared from 25.9% of a 40% solution of F10 resin; 38.2% titanium dioxide; 19.1% of China Clay; 15.4% Solvent 150; and 1.4% flow agent (Fx 32)(I.C.I.). This layer was printed as ¼" squares over the primary and secondary indicator dots layer 72 using a T77 mesh polyester screen. PEG 600 was applied and a Polyart 2 backing was applied to seal the indicators. The sample indicators were stored at 2.2, 10, 20, and 30° C. and the color measured as a function of time. The results from the experiments are shown in Table III.

TABLE III

| | STORAGE TEMPERATURE | | | | | | | |
|---|---|---|---|---|---|---|---|---|
| | 2.2° C. | | 10° C. | | 20° C. | | 30° C. | |
| | REFLECTANCE METER READINGS | | | | | | | |
| TIME DAYS | with PEG | w/o PEG | with PEG | w/o PEG | with PEG | w/o PEG | with PEG | w/o PEG |
| 0 | 44 | 44 | 44 | 44 | 44 | 44 | 44 | 44 |
| .04 | | | | | | | 37 | 43 |
| .17 | | | | | | | 27 | 41 |
| .38 | | | | | | | 19 | 36 |
| .5 | 43 | 43 | 41 | 43 | 35 | 42 | 19 | 32 |
| .75 | | | | | 31 | 40 | 19 | 24 |
| 1.0 | 43 | 43 | 39 | 41 | 30 | 39 | 19 | 22 |
| 1.7 | | | 37 | 41 | 27 | 37 | 16 | 21 |
| 1.5 | | | 36 | 41 | 24 | 35 | | |
| 2.0 | | | 35 | 40 | 22 | 34 | | |
| 2.5 | | | | | 20 | 25 | | |
| 3.0 | | | 32 | 38 | 19 | 23 | | |
| 3.5 | 40 | 40 | 27 | 35 | | | | |
| 4.0 | 40 | 40 | | | | | | |
| 5.0 | 36 | 38 | | | | | | |
| 6.0 | 36 | 38 | | | | | | |
| 7.0 | 31 | 37 | | | | | | |
| 8.0 | | | 24 | 21 | | | | |
| 9.0 | | | | | | | | |
| 10.0 | 29 | 35 | | | | | | |
| 15.0 | 28 | 33 | 16 | 14 | | | | |

It will be understood that although the invention has been described and illustrated in connection with the preferred embodiments, modifications and variations apparent to one skilled in the art may be made without departing from the essence and scope of the invention as defined in the appended claims.

Interleaved two of five or theree of nine bar code formats conventionally used to include variable information including such as inventory.

What is claimed is:

1. An integrated time-temperature indicator device comprising a system of printable multilayer compatible compositions including:
   (i) at least one layer of a first composition (a) which develops a first color change as a result of a cumulative time-temperature exposure;
   (ii) at least one composition (b) that is capable of melting at a predetermined temperature; and
   (iii) at least one composition (c) capable of producing a second color change only as a result of the melting of composition (b) and wherein said second color change is combined with the first color change of composition (a) to yield an integrated color change result.

2. The indicator device of claim 1 which incorporates additionally a backing layer which contains adhesive to attach the device to a product.

3. The indicator device of claim 2 wherein the adhesive is a self-stick adhesive in combination with a removable adhesive backing liner.

4. The indicator of claim 1 which includes a barrier layer which delays the activation of composition (c).

5. The indicator device of claim 1 which contains additionally a third layer containing the composition (c).

6. The indicator device of claim 5 which contains an additional barrier layer between (c) and (b).

7. The indicator device of claim 1 in which composition (a) and (c) are combined as a unitary layer.

8. The indicator device of claim 7 in which the acetylene is 2,4-hexadiyun-1,6-bis (ethyl urea).

9. The indicator device of claim 7 in which layer (b) is polyethylene glycol.

10. The indicator device of claim 1 in which the layer (a) comprises an acetylenic compound having at least two conjugated acetylenic groups.

11. The indicator device of claim 10 in which the acetylenic compound is a co-crystallized blend of 2,4-hexadiyn-1,6-bis (ethyl urea) and 2,4-hexadiyn-1,6-bis (n-propyl urea).

12. The indicator device of claim 1 wherein the composition (c) is disodium salt of ethyl4-[p-[ethyl(m-sulfobenzyl)amino]-(o-sulfophenyl)benzylidene[-2,5-cyclohexadien-1-ylidene](m-sulfobenzyl)ammonium hydroxide inner salt+p-sulfobenzyl] & o-sulfobenzyl salts.

13. A method of monitoring the quality condition of a perishable product which comprises affixing to the perishable product the indicator device of claim 1 observing an integrated color change of said device and correlating said integrated color change to the quality condition of said perishable product to determine the quality condition of said perishable product.

14. The method of claim 13 in which compositions of step (b) melts at the predetermined temperature and allows the composition of (c) to alter the color of (a).

15. The method of claim 13 in which the composition (a) is an acetylenic compound.

16. A method of making an integrated multilayer indicator device which substantially more closely traces the quality condition of a product than does a unitary indicator which comprises:

(i) depositing on a substrate a first layer of a composition (a) which develops a first color change as a result of a cumulative time-temperature exposure;
(ii) applying to the layer of (i) a layer of a composition (b) that melts at a predetermined temperature, and
(iii) combining with (i) and (ii) a composition (c) that changes color with the melt of (b) when the predetermined melt temperature of the (b) is attained at which time the composition of (c) adds to the color of the composition of the layer (i) to yield the desired color which signals the quality condition of a product that has been exposed to environmental temperature variation.

17. The method of claim 16 which comprises adding to the combination additionally a layer which contains a self-stick adhesive.

18. The method of claim 17 which includes sealant layer and wherein the sealant layer comprises also an adhesive for affixing the indicator and a reference color to a product whose deterioration when exposed to environmental stimuli corresponds to the color change of (a), (b) and (c) when the product is subjected to the same environmental exposure as said indicator.

* * * * *